(12) United States Patent
Sabczynski et al.

(10) Patent No.: US 11,020,184 B2
(45) Date of Patent: Jun. 1, 2021

(54) SYSTEM AND METHOD FOR ACCURATELY DETERMINING AND MARKING SKIN INCISION LINES FOR SURGICAL INTERVENTION

(71) Applicant: KONINKLIJKE PHILIPS N.V., Eindhoven (NL)

(72) Inventors: Jörg Sabczynski, Norderstedt (DE); Kirsten Regina Meetz, Hamburg (DE); Thomas Buelow, Grosshansdorf (DE); Dominik Benjamin Kutra, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1043 days.

(21) Appl. No.: 15/021,733

(22) PCT Filed: Sep. 24, 2014

(86) PCT No.: PCT/EP2014/070338
§ 371 (c)(1),
(2) Date: Mar. 14, 2016

(87) PCT Pub. No.: WO2015/044184
PCT Pub. Date: Apr. 2, 2015

(65) Prior Publication Data
US 2016/0228191 A1    Aug. 11, 2016

(30) Foreign Application Priority Data

Sep. 24, 2013   (EP) .................................... 13185725

(51) Int. Cl.
*A61B 34/10*    (2016.01)
*B43K 24/02*    (2006.01)
(Continued)

(52) U.S. Cl.
CPC ............ *A61B 34/10* (2016.02); *A61B 5/0077* (2013.01); *A61B 17/32093* (2013.01);
(Continued)

(58) Field of Classification Search
CPC ......... A61B 34/10; A61B 34/25; A61B 34/20; A61B 17/32093; A61B 5/0077;
(Continued)

(56) References Cited

U.S. PATENT DOCUMENTS 5,715,836 A * 2/1998 Kliegis ............... G06F 19/3437
600/425
5,871,018 A * 2/1999 Delp ................... A61B 17/154
128/898
(Continued)

FOREIGN PATENT DOCUMENTS

| CN | 102415896 A | 4/2012 |
|---|---|---|
| CN | 102462506 A | 5/2012 |
| DE | 20306638 U1 | 6/2003 |

OTHER PUBLICATIONS

Mears "Visibility of Surgical Site Marking After Preoperative Skin Preparation" EPlasty 2008 pp. 364-369 (Year: 2008).*
(Continued)

*Primary Examiner* — Amy R Weisberg (57) ABSTRACT

The present invention relates to a method of calculating a surgical intervention plan. Based on surface data of the patient, a surface representation of a part of the patient's body is created. From a database, a plurality of surgical methods may be selected and the geometrical parameters of a surgical plan can be adapted based on each individual surgical method. Therefore, the surgeon may easily select, which of the surgical method is appropriate for the planned surgical intervention. Furthermore, the surgical intervention plan which has been adapted according to the finally selected surgical method may then be projected onto the skin
(Continued)

of the patient such that a drawing of the incision lines is facilitated. Furthermore, the use of a remotely activatable pen based on the current position of the pen and based on the finally selected surgical plan is presented.

17 Claims, 7 Drawing Sheets

(51) Int. Cl.
*B43K 29/10* (2006.01)
*B43K 29/00* (2006.01)
*B43K 29/08* (2006.01)
*A61B 5/00* (2006.01)
*A61B 17/3209* (2006.01)
*A61B 17/00* (2006.01)
*A61B 90/00* (2016.01)
*A61B 34/20* (2016.01)
*A61B 34/00* (2016.01)

(52) U.S. Cl.
CPC .............. *B43K 24/02* (2013.01); *B43K 29/00* (2013.01); *B43K 29/004* (2013.01); *B43K 29/08* (2013.01); *B43K 29/10* (2013.01); *A61B 34/20* (2016.02); *A61B 34/25* (2016.02); *A61B 2017/008* (2013.01); *A61B 2017/00792* (2013.01); *A61B 2017/00796* (2013.01); *A61B 2034/101* (2016.02); *A61B 2034/104* (2016.02); *A61B 2034/105* (2016.02); *A61B 2090/366* (2016.02); *A61B 2090/395* (2016.02); *A61B 2090/3908* (2016.02)

(58) Field of Classification Search
CPC ........ A61B 2034/105; A61B 2034/104; A61B 2090/3908; A61B 2090/395; A61B 2090/366; A61B 2017/00796; A61B 2017/008; A61B 2017/00792; A61B 2034/107; A61B 2034/101–107; B43K 24/02; B43K 29/00; B43K 29/004; B43K 29/10; B43K 29/08; B43K 2034/105; G16H 50/00; G16H 50/50
See application file for complete search history.

(56) References Cited

U.S. PATENT DOCUMENTS

| | | | |
|---|---|---|---|
| 6,360,116 B1* | 3/2002 | Jackson, Jr. | A61N 5/1027 600/427 |
| 7,542,791 B2 | 6/2009 | Mire et al. | |
| 8,428,315 B2 | 4/2013 | Suetens et al. | |
| 9,763,746 B2* | 9/2017 | Deichmann | A61B 34/20 |
| 2005/0059873 A1 | 3/2005 | Glozman et al. | |
| 2005/0094147 A1* | 5/2005 | Yaroslavsky | A61B 5/0059 356/417 |
| 2005/0195587 A1 | 9/2005 | Moctezuma De La Barrera et al. | |
| 2006/0020279 A1* | 1/2006 | Chauhan | A61B 90/36 606/167 |
| 2007/0161907 A1 | 7/2007 | Goldman et al. | |
| 2007/0208234 A1* | 9/2007 | Bhandarkar | A61B 19/52 600/300 |
| 2011/0160578 A1 | 6/2011 | Tripathi et al. | |
| 2012/0050330 A1 | 3/2012 | Iizuka et al. | |
| 2012/0116374 A1 | 5/2012 | Jia et al. | |
| 2012/0130490 A1 | 5/2012 | Dominique et al. | |
| 2013/0060123 A1 | 3/2013 | Mordaunt et al. | |
| 2013/0072784 A1* | 3/2013 | Velusamy | A61B 17/3403 600/424 |
| 2013/0197878 A1 | 8/2013 | Fiege et al. | |
| 2014/0228860 A1* | 8/2014 | Steines | A61F 2/30942 606/130 |
| 2014/0369584 A1* | 12/2014 | Fan | A61B 6/501 382/131 |
| 2015/0305828 A1* | 10/2015 | Park | G09G 5/14 345/629 |
| 2016/0045317 A1* | 2/2016 | Lang | A61F 2/30942 700/98 |

OTHER PUBLICATIONS

Creighton "Medical Photography: Ethics, Consent, and The Intersex Patient" BJU International 2002 pp. 67-72 (Year: 2002).*
Nakajima "Computer Assisted Surgical Planning for Cerebrovascular Neurosurgery" Neurosurgery 1997 pp. 403-410 (Year: 1997).*
Henry Schein, "Axis three 3D imagining for breast procedures", Mar. 13, 2013, p. 1 http://www.henryschein.com/us-en/images/Medical/12MS6370AestheticGuide_lr.pdf.
Henry Schein, "Axis three 3D imaging for facial procedures", Feb. 16, 2011, p. 1 http://www.henryschein.com/us-en/images/Medical/12MS6370AestheticGuide_lr.pdf.
Prowess Inc., "Prowess Panther Dao IMRT Workflow", Mar. 1, 2011.

* cited by examiner

SYSTEM AND METHOD FOR ACCURATELY DETERMINING AND MARKING SKIN INCISION LINES FOR SURGICAL INTERVENTION

CROSS-REFERENCE TO PRIOR APPLICATIONS

This application is the U.S. National Phase application under 35 U.S.C. § 371 of International Application No. PCT/EP2014/070338, filed on Sep. 24, 2014, which claims the benefit of European Patent Application No. 13185725.2, filed on Sep. 24, 2013. These applications are hereby incorporated by reference herein.

FIELD OF THE INVENTION

The present invention relates to surgical intervention planning. In particular, the present invention relates to method of calculating a surgical intervention plan, a computer program element, a computer readable medium and an apparatus for calculating a surgical intervention plan.

BACKGROUND OF THE INVENTION

Breast cancer is the most common cancer to affect women. Surgical treatment of breast cancer, i.e. excision of the tumour, often is the main treatment for breast cancer. The standard procedure is a partial or complete removal of the breast (mastectomy). Breast conserving surgery followed by radiation therapy is an alternative, which is comparable with respect to tumour control. Oncoplastic surgery is the combination of oncologic surgery for tumour resection with plastic surgery procedures for the reconstruction of the breast. It results in cosmetically acceptable results.

In order to prepare a breast conserving or oncoplastic procedure, drawings are done pre-operatively on the skin with the patient in an upright standing position. The size of the tumour is drawn, as well as lines to indicate the future position of the nipple and lines for skin incisions. These pre-operative drawings are used by the surgeon during the procedure for orientation. In order to verify that the planned skin incisions fit together, their length may be verified with the help of a tape measure.

Several problems are connected to the method described above. The complete pre-operative planning is done on the skin of the patient, which might be difficult for the patient. The planning is done with a marker pen and therefore, the drawing is difficult to change. Consequently, it is difficult to test different surgical approaches. Measurements must be done with a tape measure and the position and size of the tumour is only roughly known during drawing. Moreover, in brain surgery, the patient is usually fixed to the operation table with the help of an invasive clamp. The head is often shaved. Before the surgery begins, the position of the planned incision is drawn with a pen onto the skin. If stereotactic surgery is performed this is done with the help of a surgical navigation system. These systems consist of a computer, a position measurement device, and tracked instruments. Usually, navigation systems can be used with a pointing instrument, which allows pointing to the patient and seeing its position in the patient's image (e.g. CT/MR slices or reconstructed 3D image) on a computer screen.

The operator now tries to find and point to the line of the planned incision on the patient with the pointing instrument. During this procedure he looks at the navigation system's computer screen. Once he has found a point on the incision line, he looks at the patient and at his hand with the pointing instrument, takes a pen, and marks the found point with the pen. This procedure is repeated until enough points on the planned incision line are marked and the line can be drawn onto the patient's skin by connecting the marked points. After this procedure the patient is sterilely covered leaving free the operating field and the operation begins.

SUMMARY OF THE INVENTION

The object of the present invention may be seen as providing an improved surgical planning.

The object of the present invention is solved by the subject-matter of the independent claims. Further embodiments and advantages of the invention are incorporated in the dependent claims.

The described embodiments similarly pertain to method of calculating a surgical intervention plan, the computer program element, the computer readable medium and the apparatus for calculating a surgical intervention plan. Synergetic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. The skilled person gathers all kinds of different orders and combinations of the method steps described herein, unless explicitly mentioned to the contrary hereinafter.

According to an exemplary embodiment of the present invention, a method of calculating or creating a surgical intervention plan is presented. The method comprises the step of receiving data of a patient's surface, receiving data of a planned surgical intervention and creating a surface representation of a part of the patient's body based on the received data of a patient's surface. Moreover, selecting a first surgical method out of a plurality of parameterized surgical methods stored in a database is comprised as well as adapting geometrical parameters of a surgical intervention plan based on the selected first surgical method thereby calculating an adapted surgical intervention plan. Further, the step of displaying the adapted surgical intervention plan to the user is also comprised by the presented method.

In other words, a planning method for surgical interventions is presented which allows testing different surgical techniques by a calculation process. In particular, the outcome of different surgical methods for resecting a targeted object such as a tumor or lesion, or at least part thereof, may be visualized.

Figure 4:
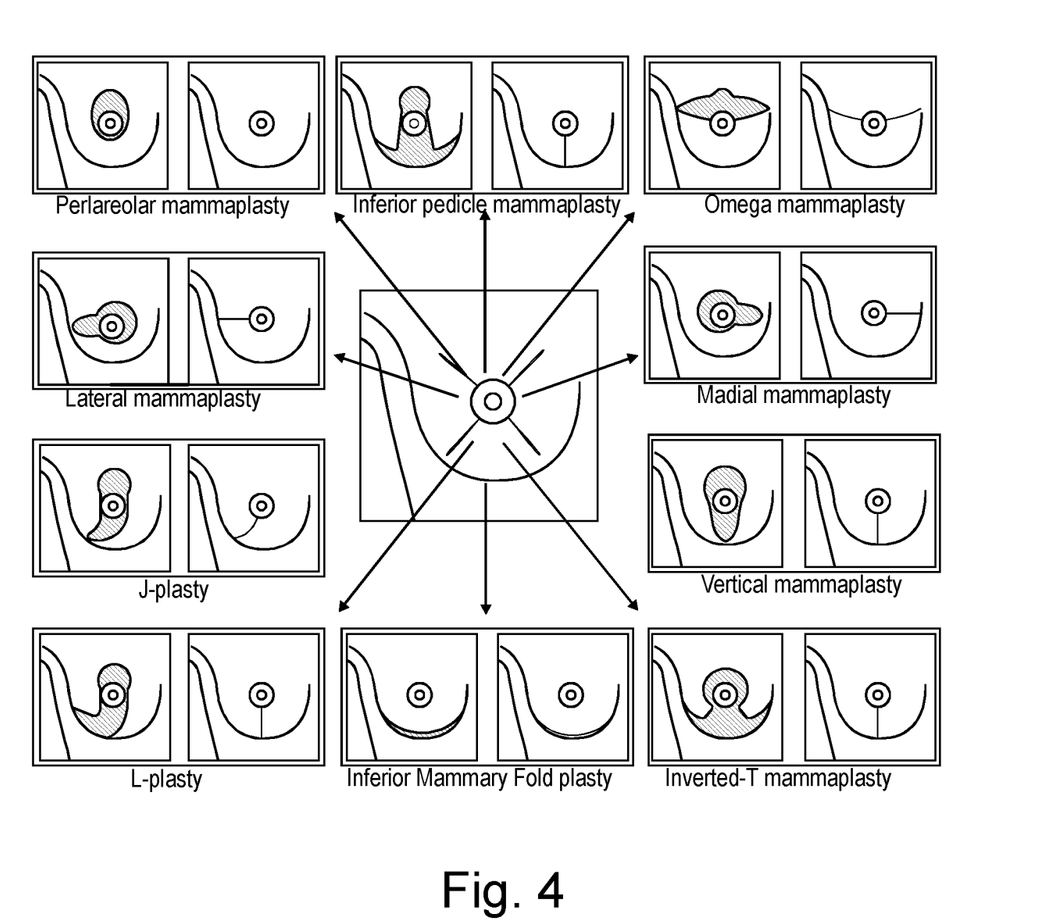
FIG. 4 schematically shows a plurality of breast surgery methods that can be stored in a database in accordance with the present invention.

The planning method may account for geometrical constraints of each surgical method, which can also be stored in the database. Moreover, this method allows for virtually drawing the different surgical techniques onto the representation of the skin of the patient such that an improved decision making is facilitated. In particular, this method may be carried out by a planning system which comprises a computer with means to visualize the planning, means to create/calculate the geometrical representation of the patient's surface, and a database of the parameterized surgical methods. According to an exemplary embodiment, FIG. 5 discloses exemplary workflow of such a method in a corresponding system and FIG. 4 shows different examples surgical breast methods. As will become apparent from and elucidated with the following description, the invention can be used in, for example, plastic surgery, oncoplastic surgery, breast conserving surgery and also in other surgical fields.

As will be explained in more detail herein, the data of the patient's surface, which can be provided for example as data from a surface scanner and/or from an imaging device, are used to calculate the surface representation of the part of the patient's body.

Furthermore, providing the database which comprises the plurality of surgical methods, i.e., data of or about the surgical method, respectively, may also be comprised by the presented method. If desired, the step of displaying the adapted surgical intervention plan to a user may also be part of the presented method.

The term "intervention data of/about a planned surgical intervention" can be embodied in various different ways. For example, this feature may specify what kind of intervention is planned by the surgeon, i.e., a breast surgery or a brain surgery. Additionally, the intervention data comprises data representing a targeted object, for example an object to be resected such as a tumour or lesion. For example, the intervention data may include the exact tumour location and/or the tumour shape. Hence, data which define the location of a tumour and/or tumour shape may be seen as data of/about a planned surgical intervention. However, in case it is desired to extract healthy tissue during a surgical intervention, also the location and/or shape of the targeted tissue which is healthy may be seen as an embodiment of the intervention data of a planned surgical intervention. In an exemplary embodiment, the location and/or shape of a targeted object, like targeted tissue or the location of a tumour, is used. The targeted object may also be, for example, an organ or a vessel of the patient.

It should be noted, that in the context of the present invention the steps of receiving of data can also be understood as providing and/or retrieving the respective data. Furthermore, the step of adapting the geometrical parameters of a surgical intervention plan may be understood to comprise the creation of such a plan by calculation. Further, also the retrieval of the initial surgical intervention plan from, for example, a database or from a user input shall be comprised.

Further, the adaption is based on the data of a planned surgical intervention and the created surface representation. Thus, the system which calculates the adaptation of the geometrical parameters may firstly take into account the first surgical method selected by the user, may secondly take into account the intervention data of/about the planned surgical intervention, like, e.g., the tumour location and/or tumour shape, and may thirdly take into account the surface representation that has been calculated before.

The term of "adapting geometrical parameters" may be understood as changing the geometrical parameters in the visualized form of the plan. The calculation of the surface representation may be carried out by the same system that calculates the adaption, but also another device or system can be used for this purpose. The adapted intervention plan can be shown to the user based on the adapted geometrical parameters.

The parameters of the surgical method and the individual surgical plan may be, for example, one or more angles between resection lines, the lengths of the resection lines, and/or the depth of resection lines. Furthermore, application specific parameters may be used. For example, in the exemplary case of breast surgery the size of the areola, the distance between current and future nipple position are parameters that can be used to geometrically define a surgical plan in general. Individual values of said parameters then define a concrete and individual surgical intervention plan. More explanations and details about such geometrical parameters of a surgical plan will be provided in the following and exemplary embodiments thereof will be discussed in the context of FIGS. 3 and 4. Said parameters are adapted based on the selected surgical method. In general, mathematical parameters like angles, coordinates and/or parameters defining incision lines, particularly the length and depth thereof, can be used in the context of the present invention to parameterize surgical methods and intervention plans.

The geometrical constraints of a surgical method or plan can be seen as boundary values or threshold values of a parameter used in a specific surgical method or plan. For example, in a specific breast surgery method the depth of an incision line cannot increase a certain value, like, for example 3 mm. The geometrical constraints can also be seen as relationships between the parameters of the plan as explained in the context of FIG. 3. In the context of this specific embodiment it is explained that the length of incision/cut 304 should be twice the length of incision/cut 305. Further, the length of cut/incision 306 left should equal the length of cut/incision 306 right. This may be seen as an example of relationships between the parameters of the surgical method in form of geometrical constraints.

According to another exemplary embodiment of the invention, at least one geometrical constraint of the first surgical method is retrieved from the database. Moreover, the method further comprises the step of automatically taking into account the geometrical constraint of the first surgical method during the adaption of the geometrical parameters of the surgical intervention plan.

Figure 3:
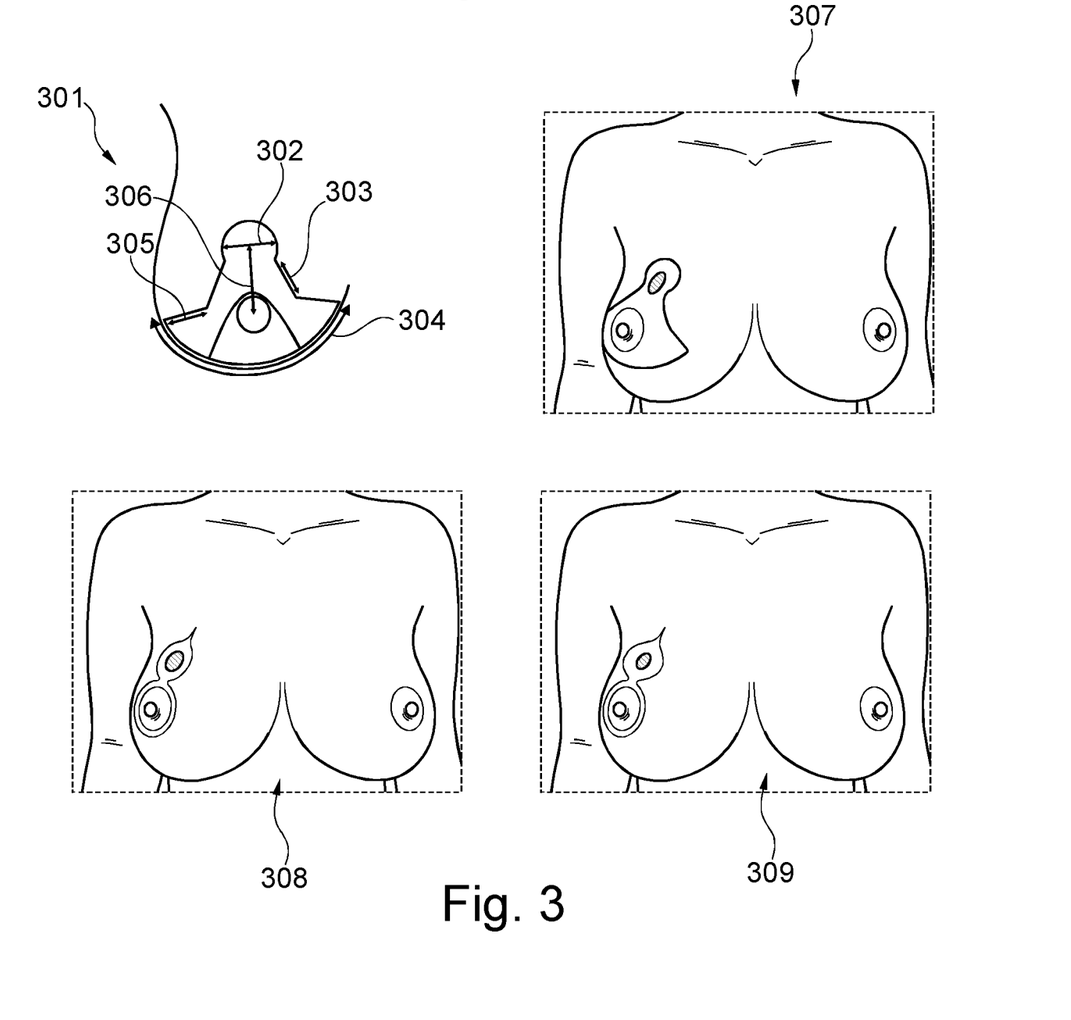
FIG. 3 schematically shows how a surgical plan may be geometrically parameterized as used in an example in accordance with the present invention.

Examples of such geometrical constraints can be seen in FIG. 3. In a specific embodiment the length of incision/cut 304 should be twice the length of incision/cut 305. The length of cut/incision 306 left should equal the length of cut/incision 306 right. Moreover, the length of the circular cut should equal the circumference of the areola.

According to another exemplary embodiment of the present invention, the step of creating the surface representation of the part of the patient's body comprises surface triangulation and texture mapping.

In other words, 3D surface rendering can be comprised by the present invention. For example, raw data of the patient's surface can initially be captured, e.g. as photos or as surface scans. Based on these raw data, the surface representation by triangulation can be created. Photos retrieved from a camera are used to color the surface representation realistically, which is understood in the context of the present invention as texture mapping. This may increase the accuracy of the calculated intervention plan.

According to another exemplary embodiment of the invention, the surgical intervention plan is displayed to the user in form of at least a line of a skin incision in/on the created surface representation of the part of the patient's body.

The future skin incision lines may be understood as lines which provide the surgeon with a guidance for the steps of incising the skin of the patient. This allows testing different surgical techniques by drawing the pre-operative planning virtually onto the skin of the patient by drawing and/or projection the different results onto the representation of the skin. For example, such future skin incision lines can be projected onto the patient for verification and illustration purposes.

According to another exemplary embodiment of the invention, the surgical intervention plan comprises at least one line of a future skin incision on the breast of the patient, wherein the created surface representation describes a shape of the patient's breast and the method further comprises the step of automatically adapting the line of a future skin incision of the surgical intervention plan to the shape of the patient's breast.

In other words, this embodiment may be seen as a method of calculating a breast surgery intervention plan, wherein a desired skin incision on the breast of the patient is calculated and displayed on the surface representation of the patient's breast.

Such incision lines may not only be located on the surface of the skin, but may have a certain depth into the body of the patient, i.e., into the breast of the patient. For example, a tumour may not only be described by its location, but also by its shape in a three dimensional manner. This may be taken into account for the planning and calculation of the incision lines in the context of the present invention.

According to another exemplary embodiment of the invention, the method comprises the steps of receiving a user input which is configured to trigger a change of the geometrical parameters of the surgical intervention plan, and adapting the geometrical parameters of the surgical intervention plan based on the received user input. Moreover, displaying the adapted surgical intervention plan to the user is comprised by the method.

In other words, an interactive feature analyzer is presented. The surface representation is visualized and feature points and lines can then be interactively identified by the planning surgeon, e.g. with a mouse-based user interface, or other interface means.

According to another exemplary embodiment an automatic feature analysis is comprised.

This method step can be is used to detect features in the surface representation, for example in case of breast surgery, the nipple position, nipple diameter, symmetry line, clavicular position, position of the infra-mammary fold. A corresponding feature analysis device may be used for this purpose, as described in the embodiment of FIG. 5.

According to another exemplary embodiment of the present invention, scanning the part of the patient's body with a surface scanner, and capturing a photo of the part of the patient's body thereby providing the data of the patient's surface is comprised.

Different aspects about surface scanning, photo capturing, installation, calibration, generation of planning input and the transfer of the surgical plan will be presented in detail hereinafter. The data generated by the scanning process and by the photo process can be used for the triangulation and texture mapping. The surface representation may be calculated based on these data. More details about this aspect of the present invention will be disclosed in the context of specific embodiments, in particular in the context of FIGS. 2, 5, 6 and 7.

According to another exemplary embodiment of the present invention, selecting a second surgical method out of the plurality of surgical methods stored in the database is comprised. Further, adapting the geometrical parameters of the surgical intervention plan based on the second selected surgical method and displaying the surgical intervention plan to a user in form of at least a line of a future skin incision shown in/on the created surface representation of the patient's breast is comprised.

In other words, an iterative scanning method is presented by means of which the user may sequentially select at least two different surgical techniques and may evaluate the first and the second techniques based on the displayed respective surgical plan. Such an iterative aspect of the present invention is comprised, inter alia, in the embodiment of FIG. 5.

According to another exemplary embodiment of the present invention, the step of interactively defining a position of a targeted object (i.e. a targeted object's position) and/or a targeted object resection margin or importing a targeted object's position and/or a targeted object resection margin from a workstation.

This step may be seen as part of the step receiving data of the planned surgical intervention as defined before. The user may define or provide such an input, like e.g. the position of the targeted object, in various ways and by means of different devices. A pre-operative imaging dataset, e.g. MRI or CT, can be used as explained in the context of FIG. 5, but the user may also provide coordinates of the targeted object in a numerical format as a data set. Also other input variants are possible. The targeted object may also concern different organs or structures like tissue structure and may be visualized in the calculated surface representation. In particular, structures which are positioned underneath the surface of the skin can be visualized.

The position of the targeted object, i.e. the targeted object's position may be seen as the position of an organ or the shape of an organ, the position of a lesion, the shape of a lesion and the object may also be understood as a structure or a vessel of the body. Further, an organ position, a shape of an organ, a lesion position, and/or a lesion shape can be defined interactively.

According to another exemplary embodiment of the present invention, the method comprises the step of projecting the adapted surgical intervention plan onto the part of the patient's body.

Thus, the surgical plan can be transferred to the patient by the projection. A projection calculator software may use data from a surface scan of the patient's body and may also use calibration information to calculate the projection of the surgical plan onto the patient's surface. More details about this aspect will be explained in the context of FIG. 6 and FIG. 7. It should be noted that this embodiment can be used in accordance with the calculation method as defined before and hereinafter. However, also the projection of a surgical plan that is provided somewhat differently is disclosed herewith. This holds also true for the projection aspects disclosed in the context of FIGS. 6 and 7.

The geometrical properties or characteristics of the projector should be known, i.e., it should be known to the user which beam (which may be defined by the direction and a starting point in space) the projector uses for projecting a specific pixel of the image. This may be determined by an appropriate calibration method. The position and orientation of the patient relative to the projector should also be known. This may be determined by a measurement with a surface scanner. In a preferred embodiment as described herein, the surface scanner and projector are provided together in one single device such that the geometrical parameters are not changed and need to be determined only once. The position and orientation of the patient surface underlying the geometric parameters used in the surgical intervention plan may then be adapted to the measured surface of the patient in an optimization step. Therefore, the position of the cuts/incisions in space relative to the projector are known and the calculation of the image, which is to be projected, has a decreased complexity, while ensuring that the surgical interventional plan is shown on the patient in a correct manner.

In combination with such a projection, phosphorescent material dispensed on the body of the patient can be used which is then excited by the projection light and the user may take advantage of the excited and light emitting molecules on the skin of the patient showing the surgical plan. This may facilitate an improved transfer of the calculated plan on the skin of patient.

According to another exemplary embodiment of the invention, the method comprises the steps of scanning the surface of the part of the patient's body with a surface scanner thereby generating surface data, i.e. data of the patient's surface.

According to another exemplary embodiment of the invention calculating projection data for projecting the adapted surgical intervention plan onto the part of the patient's body based on the surface data is comprised.

Figure 7:
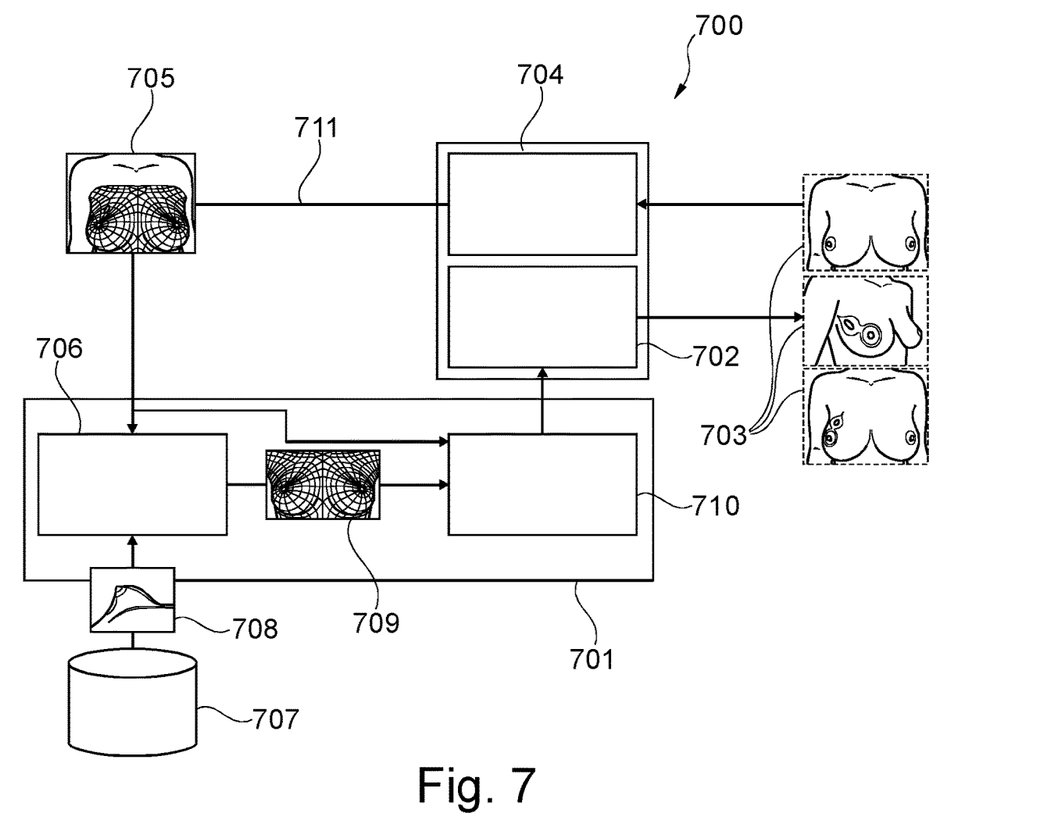
FIG. 7 schematically shows an apparatus with a scanner and a projector and the workflow according to another exemplary embodiment of the present invention.

In a corresponding exemplary embodiment an apparatus or system as shown in FIG. 7 may carry out such a method. Advantageously, such a method allows for transferring the projected and adapted surgical intervention plan onto the body of the patient by marking thereby increasing the accuracy of the transfer of the calculated plan on the patient's body.

According to another exemplary embodiment of the invention, an activation signal is sent to a remotely activatable marking pen thereby activating the pen based on the adapted surgical intervention plan.

For example, the control unit as defined herein may be configured for activating the pen when the measured position of the pen matches a line or corresponds to a line as defined in the adapted surgical intervention plan. In other words, an automatic drawing apparatus can be used which allows the surgeon to easily draw the pre-operative computer-based planning onto the patient's skin based on and in accordance with the previously calculated interventional plan. Thus, a tracked and active pen is used for drawing the incision line onto the skin of the patient. Therefore, it is much easier, faster and more accurate to produce a drawing of the planned incision line on the patient's skin. In this way, the pen can draw only at positions, which correspond to the predefined surgical intervention plan. A corresponding example of a pen and an apparatus/system for a signal generation and transmittal based on the location of the pen and the calculated plan is depicted and explained in the context of FIG. 9. Such a system automatically creates a drawing (or a 3D surface representation) of the calculated surgical plan on the skin of the patient with a high accuracy.

It should be noted that this embodiment can be used in accordance with the calculation method as defined before and hereinafter. However, also a use of this remote activation of the pen which is based on the position of the pen in combination with a surgical plan that is provided somewhat differently is disclosed herewith.

According to another exemplary embodiment of the present invention, the position of the pen on a surface of the patient is measured and the pen is activated if the measured position of the pen corresponds to a line of the adapted surgical intervention plan.

This method may be carried out by a device that measures positions and creates a drawing or a 3D surface representations of the surgical intervention plan. The planning of the incisions can be done based on patient images or can be carried out by the method as defined herein. A tracked and active pen can be used for drawing the incision line. The position of the tracked and active pen can be measured by the position measurement device. In this respect, the pen replaces the pointing instrument of the navigation system of state of the art systems. Furthermore, in this embodiment of the present invention, drawing capabilities of the active pen can be switched on and off by the apparatus which comprises the sender. A computer software may control the tip of the device in such a way, that whenever the tip of the active pen is on the incision line, drawing is switched on. And whenever it is not on an incision line, the drawing is switched off by the sender. An exemplary embodiment of such a system is shown and explained in the context of FIG. 9.

According to another exemplary embodiment of the invention, activating a retraction unit of the pen is comprised by the method.

According to another exemplary embodiment of the present invention, an apparatus for calculating a surgical intervention plan is presented. The apparatus comprises a receiving unit for receiving data of a patient's surface and data of a planned surgical intervention. Moreover, a calculation unit, a display unit, an interface and a database is comprised. The calculation unit is configured for creating a surface representation of a part of the patient's body based on the received data of the patient's body. Moreover, the interface is configured for receiving a user input which is a selection of a first surgical method out of a plurality of parameterized surgical methods stored in the database. Moreover, the calculation unit is configured for adapting geometrical parameters of a surgical intervention plan based on the selected first surgical method and for calculating the adapted surgical intervention plan. Furthermore, the display unit is configured for displaying the adapted surgical intervention plan to the user.

Exemplary embodiments of such an apparatus will be described in more detail with respect to FIGS. 5, 7, 8 and 9. In general, such apparatuses can be configured by the user to carry out the various different methods described herein.

According to another exemplary embodiment of the invention, a surface scanner and a projection device is comprised by the apparatus. The surface scanner is configured for scanning the surface of the part of the patient's body thereby generating surface information. The projection device is configured for projecting the adapted surgical intervention plan onto the part of the patient's body.

More exemplary details about such apparatuses will be given in the context of FIGS. 6 and 7 and aspects of corresponding method embodiments are also disclosed herein.

According to another exemplary embodiment of the invention, the apparatus is configured for activating a remotely activatable pen based on the adapted surgical intervention plan.

In other words, the desired and calculated surgical intervention plan may be used as a basis for activating the remotely activatable pen taking into account the current position of the pen. In other words, the drawing capabilities of the pen can be switched on and off by this apparatus. This apparatus can control the tip of the pen in such a way that whenever the tip of the pen is on the incision line when guided over the skin of the patient, drawing is switched on. And whenever the pen is not on the incision line, the drawing is switched off.

In an exemplary embodiment, the apparatus comprises a sender, the remotely activatable pen with a receiver, and a control unit. Therefore, the pen is embodied separately from the rest of the apparatus. The control unit is configured for controlling the sender such that the sender sends an activation signal to the receiver of the pen thereby activating the pen based on the adapted surgical intervention plan and on the current position of the pen.

In other words, in an exemplary embodiment a system for calculating a surgical intervention plan is presented. The system comprises the apparatus as described before and hereinafter, wherein the apparatus further comprises a sender and a control unit. This system further comprises the remotely activatable pen which comprises a receiver. Further, the control unit is configured for controlling the sender such that the sender sends an activation signal to the receiver of the remotely activatable pen thereby activating the pen based on the adapted surgical intervention plan. More details and specific embodiments thereof will be described in and elucidated with the context of FIG. 9.

According to another exemplary embodiment of the invention the use of a phosphorescent material, e.g. a powder or gel, on the patient's skin in order to retain a visible image of the projected surgical plan after the projection is finished, is presented.

A possible workflow for copying a computer generated plan onto the patient's skin according to the proposed invention will be described in the following. A computerized surgical plan is developed either automatically or interactively and adapted to the patient's anatomy according to the herein described methods and apparatuses. The patient is prepared by covering the breast by either phosphorescent powder, or a clear gel containing such powder. Also other phosphorescent materials may be used.

For example, a commercially available non-toxic "Europium UltraGlow Powder" can be used, but also other materials are suitable for the purpose described herein. The projection device is used in order to project the plan for a short time at high intensity onto the patient's body. Alternatively the projection device is modified by incorporating a laser device tracing the lines contained in the surgical plan. A UV-laser can be used in order to activate the phosphorescent powder. Also other light sources may be used to activate the phosphorescent material. At the sites of the lines and markers contained in the surgical plan, the phosphorescent powder is activated by the UV-laser or the UV-component contained in the light used by the plan projector.

By the activation of the phosphorescent powder at the sites of the projected markers these remain visible on the patient's skin even when the patient moves or when the breast is deformed. This visibility of the plan might only be achieved for a limited time under dimmed light conditions. In order to capture the plan permanently it can be traced by the surgeon with a permanent marker.

It may be seen as a gist of the invention to provide for a planning system for surgical interventions allows the surgeon to do the preoperative planning and drawing on the computer. It allows testing different surgical techniques by drawing them virtually onto the skin. The system may automatically take into account geometrical constraints of the surgical plans. In a further aspect of the present invention, a planning and projection system for surgical interventions is provided which allows additionally for an easy transfer of the planning result from the computer as drawings onto the patient's skin. In a further aspect a remotely activatable pen is activated based on the current position of the pen and based on the calculated interventional plan such that the calculated plan is transferred by the pen on the skin vie controlled marking.

These and other features of the invention will become apparent from and elucidated with reference to the embodiments described hereinafter.

DETAILED DESCRIPTION OF EMBODIMENTS

Figure 1:
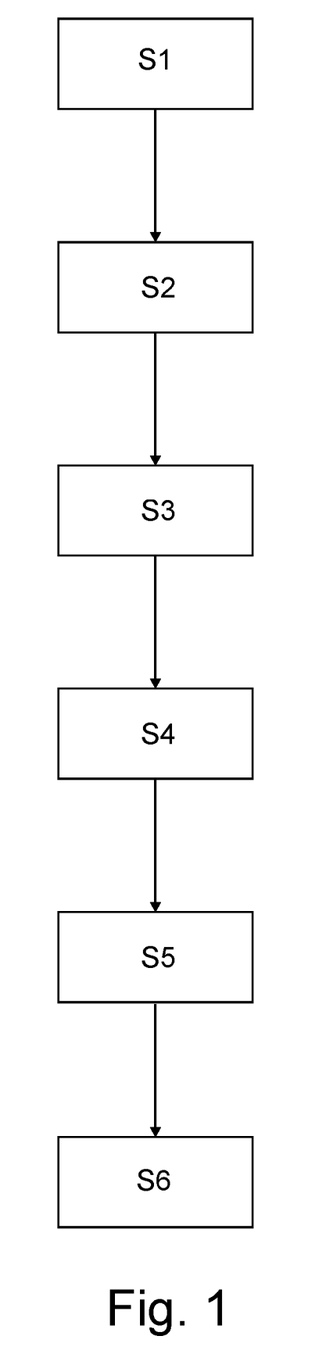
FIG. 1 schematically shows a flow diagram of a method of calculating a surgical intervention plan according to an exemplary embodiment of the invention.

FIG. 1 shows a flow diagram of a method of calculating a surgical intervention plan according to an exemplary embodiment of the invention. In step S1 data of a patient's surface are received, provided, or retrieved and in step S2 data of a planned surgical intervention are provided or retrieved. Moreover, a surface representation of a part of the patient's body based on the received data is created in step S3. Selecting a first surgical method out of a plurality of parameterized surgical methods that are stored in a database is carried out in step S4 and geometrical parameters of a surgical intervention plan are adapted based on the selected first surgical method in step S5. Further, the step of displaying the adapted surgical intervention plan to the user is also comprised by the presented method and shown with S6.

A specific example of this embodiment in the field of breast surgery will be described in the following. Raw data of a patient's surface is captured as photos and/or surface scans. Then a surface representation of the thorax and breasts is created, thereby using triangulation. To this, feature points are added like, for example, the nipple positions, the nipple diameter, the symmetry line, the clavicular position, the position of the infra-mammary fold, and/or tumour data such as the tumour position and/or resection margins can be added as well. This may be done interactively by the user or automatically by the apparatus using a shape and image feature analyzer. Then, the surgeon triggers a selection of a surgical method from a database, which selection is carried out by the system. Geometrical parameters of the corresponding plan are adapted and represented in a parameterized fashion. If the surgeon is comfortable with the resulting plan, it can be visualized and stored for transfer into the operating room. More details can be gathered from the exemplary embodiment of FIG. 5.

Another specific example of the embodiment of FIG. 1 will be described hereinafter. This example relates to capturing a patient's surface and projecting the planning result back to this surface, for example by the abovementioned apparatus. Phosphorescent materials as described herein may then be used for transferring the plan on the skin of the patient's body. A combination of a surface scanner and a projector, i.e. a projection device, is used. As a surface scanner is employed and the projector can preferably be a pico-projector. Preferably, scanner and projector are integrated in a single device. In an initial session, the patient's surface and texture information is recorded. After the surgical plan has been calculated or selected, the plan can be transferred to the patient. The surface is re-scanned, which information is combined with the surgical plan selected. The information, optionally combined with calibration information, is projected back onto the patient's surface. The surgeon can then mark the surface with a pen thereby transferring the projected and adapted surgical intervention plan onto the body of the patient by marking. As described herein, also a remotely activatable pen or a phosphorescent material dispensed on the body of the patient can be used.

Further, according to another exemplary embodiment of the invention similar to FIG. 1 the step of transferring the projected and adapted surgical intervention plan onto the body of the patient by marking is comprised.

Another specific example of the embodiment of FIG. 1 may be described as follows. Base on the surgical intervention plan that has been calculated, i.e. the adapted surgical plan provided after one or more iterations of the method, a remotely activatable pen is activated depending on its current position. More details about this aspect can be gathered from, for example, FIG. 9.

Further, the method of FIG. 1 may also comprise the steps of localizing a position of a targeted object of the patient's body in the created surface representation, and visualizing the localized position of the targeted object in the created surface representation.

Moreover, the method described in FIG. 1 may, for example, make use of the following surgery methods, which are mentioned as non limiting embodiments. The plurality of surgical methods can be chosen from the group comprising periareolar mammaplasty, inferior pedicle mammaplasty, omega mammaplasty, lateral mammaplasty, medial mammaplasty, J-plasty, vertical mammaplasty, L-plasty, inferior mammary fold plasty, inverted-T mammaplasty, batwing method, and any combination thereof. Of course other interventional techniques and surgery methods, that are parameterized can be used. The principle of parameterization is explained in detail herein, for example in the context of FIGS. 3 and 4.

Furthermore, a program element for calculating a surgical intervention plan and a computer-readable medium, in which a computer program for calculating a surgical intervention plan is stored, is comprised by the present invention. These embodiments are in line with the method as has been described before, in particular in the context of FIG. 1.

Said computer program element may be part of a computer program, but it can also be an entire program by itself. For example the computer program element may be used to update an already existing computer program to get to the present invention. A computer program may be stored/distributed on a suitable medium such as an optical storage medium or a solid-state medium supplied together with or as part of other hardware, but may also be distributed in other forms, such as via the Internet or other wired or wireless telecommunication systems.

The computer readable medium may be seen as a storage medium, such as for example, a USB stick, a CD, a DVD, a data storage device, a hard disk, or any other medium on which a program element as described above can be stored. A single processor or other unit may fulfill the functions of several items or steps recited in the claims. Examples of such a program element for calculating a surgical intervention plan and of a computer-readable medium are further shown and/or explained in the context of FIGS. 5, 7 and 8, in particular.

Figure 2:
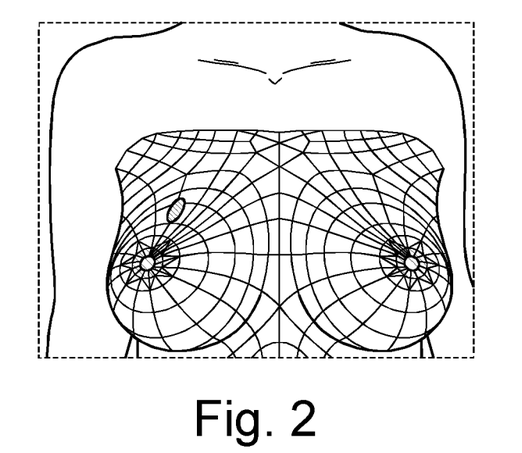
FIG. 2 shows an example of 3D surface rendering with texture mapping according to an exemplary embodiment of the present invention.

FIG. 2 schematically shows an example of how the 3D surface rendering with texture mapping may look like at a surface representation of the patient. In the context of the embodiment of FIG. 5, such a surface representation of the patient is used. In FIG. 3 the mamilla position and areola size, mid saggital symmetry line, and tumour are shown.

FIG. 3 schematically shows an example of how a surgical intervention plan can be geometrically parameterized. In picture 301 the arrows 302 to 306 show the length, orientation, and angles of geometrical elements of the plan, which can be adapted during planning. These adaptions can be caused by to a user input or can be caused by automatic calculation when taking into account the provided data of the patient's surface and data of the planned surgical intervention. In FIG. 3 is shown how at least one geometrical constraint may look like. Examples of such geometrical constraints can be seen in FIG. 3. In a specific embodiment the length of incision/cut 304 should be twice the length of incision/cut 305. The length of cut/incision 303 left should equal the length of cut/incision 303 right. Moreover, the length of the circular cut should equal the circumference of the areola. Picture 307 is a visualized calculated surgical interventional plan which is projected to or marked on the skin of the patient. In picture 307 a first surgical method has been selected out of a plurality of stored methods by the surgeon. Pictures 308 and 309 are visualization of another, different surgical method compared to FIG. 307. The difference between 308 and 309 is a different parameterization of the respective surgical plans.

FIG. 4 schematically shows different surgical methods for breast surgery. These examples are understood as non limiting examples of such breast surgery methods. The plurality of methods for breast surgery comprises periareolar mammaplasty, inferior pedicle mammaplasty, omega mammaplasty, lateral mammaplasty, medial mammaplasty, J-plasty, vertical mammaplasty, L-plasty, inferior mammary fold plasty, inverted-T mammaplasty, batwing method. These methods may also be combined by the surgeon and by the calculation apparatus. The breast surgery methods depicted in FIG. 4 are known to the skilled person and can all be parameterized based on the principles as have been described before with respect to FIGS. 2 and 3.

Figure 5:
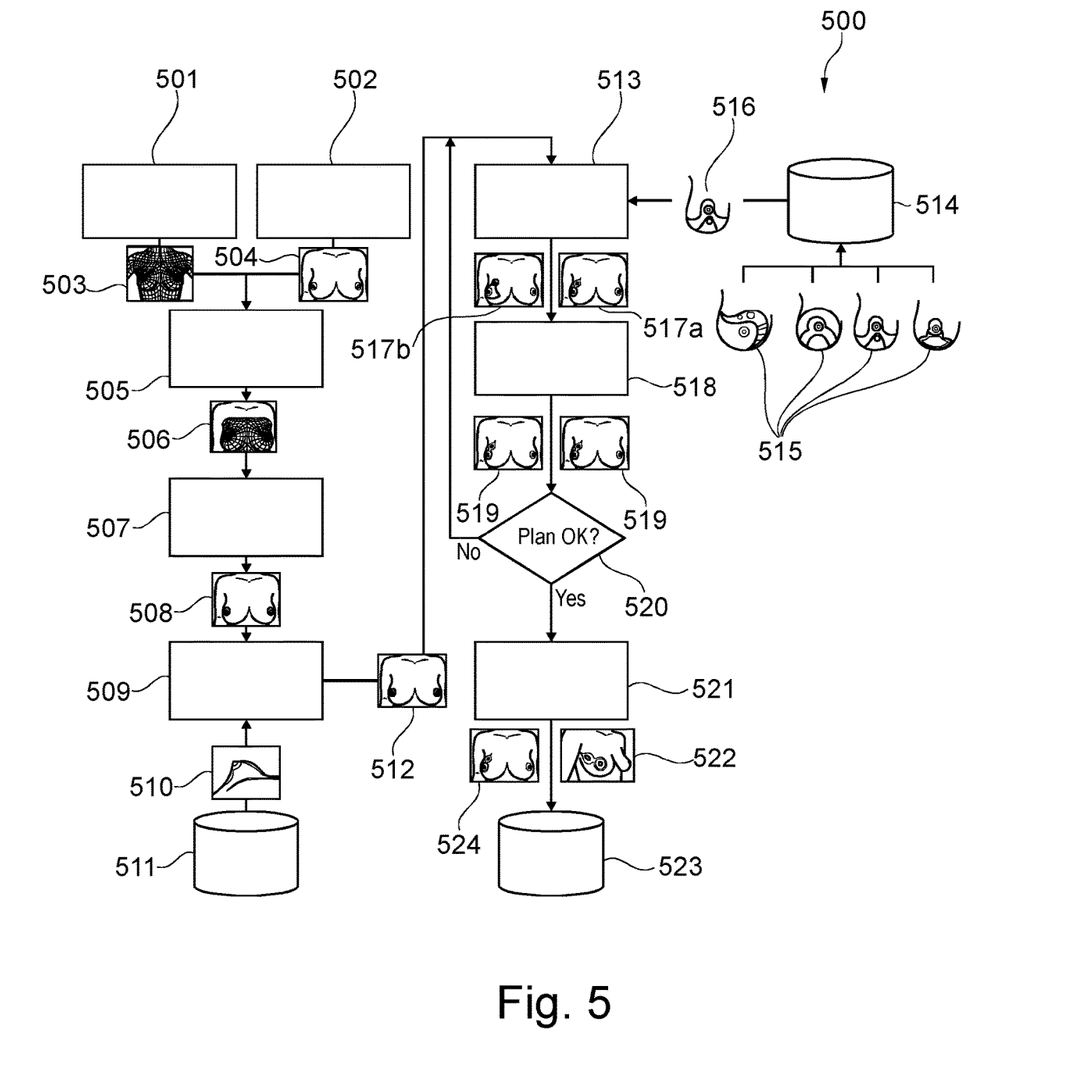
FIG. 5 shows a workflow in an apparatus in accordance with an exemplary embodiment of the present invention.

FIG. 5 schematically shows a flow diagram in an apparatus 500 for calculating a surgical intervention plan in accordance with the present invention. The apparatus 500 allows testing different surgical techniques by drawing them virtually onto the skin. The system automatically takes into account geometrical constraints of the surgical plans, as will be explained in the following. The apparatus is a planning system which comprises a computer with means to visualize the planning, means to create a geometrical representation of the patient's surface, and a database of parameterized surgical methods. In the non limiting example case of oncoplastic breast surgery, the workflow of the specific embodiment shown in FIG. 5 is as follows. Initially, raw data of the patient's surface is captured, e.g. as a photo 504 and/or as a surface scan 503 using a surface scanner 501 and/or camera 502. This can be done by several means, e.g. photographs from different angles or with the help of a dedicated surface scanning system like, for example, Microsoft's Kinect sensor. This sensor allows to measure a depth map along with a photo. Further, a shape processor 505 is provided in apparatus 500. Subsequently a surface representation of the patient's thorax is created. Based on the raw data from step 1 a surface representation 506 is created thereby using triangulation as known by the skilled person. Photos retrieved from the camera are used to color the surface representation realistically, i.e. texture mapping is applied. It should be noted that the image shown to the surgeon according to this exemplary embodiment of 506, as well as for the example given in FIG. 2, the imaging may be such that the surgeon can vary the angle of perspective and the distance to the shown object. The depiction given in 506 is used to illustrate the difference between photos and 3D models with texture mapping.

Further, the previously described steps 1 and 2 can be implemented differently, as long as the result of the raw data capture and shape pre-processing is a surface triangulation of the patient's breasts and thorax with texture mapping. It should be noted that the method may also be carried out without texture mapping, however, texture mapping may improve the illustration. The shape and feature analyzer 507 is a component of the apparatus, which is used to detect features in the surface representation, for example, the nipple position, areola diameter, symmetry line, clavicular position, position of the infra-mammary fold, etc. However, the apparatus may also be provided without the shape and feature analyzer 507. The feature analyzer can be automatic or interactive. In case of an interactive implementation, the surface representation is visualized 508 e.g. on a computer screen. Feature points and lines are then interactively identified by the planning surgeon, e.g. with a mouse-based user interface. Moreover, the tumour position and/or the tumour resection margins are either interactively defined or imported from a different workstation 511. Step 509 shows such tumour localization. If necessary, a pre-operative imaging dataset 510, e.g. MRI or CT can be used. A sketch of the result of the beforehand described steps is shown with 512.

Furthermore, the apparatus may automatically select in step 513 one of the parameterized surgical methods 515 stored in the database 514. Alternatively, the surgeon may do the selection. In this example here, method 516 is selected. Non limiting examples of such methods are given in FIG. 4 and exemplary parameterizations are explained, for example, in the context of FIG. 3. Which surgical method is the best choice may depend on several factors like tumour size and location, size of the breast, shape of the breast, patient age, patient preferences, etc. After the selection of the method or of the methods, the geometrical parameters of the corresponding surgical intervention plan are adapted by the apparatus in step 518. The surgical methods/plans are represented in a parameterized fashion, see also FIG. 3 for an example. The shape of the cut lines (incisions) is adapted to the shape of the patient's breast by the apparatus. The results after the adaption are shown to the user in 519. Here, two different adaptions of parameters of the surgical interventional plan are displayed to the user. If desired, the surgeon can also (in addition or alternatively) change interactively the geometrical parameters of the surgical plan by an input via a user interface. In this example, the parameters are the size of the areola, distance between current and future nipple position, angles between resection lines, lengths of resection lines and depth of resection. The skilled person may also make use of other parameters which he finds appropriate for the specific case. Further, if the surgeon is comfortable with the resulting surgical plan 519, it can be visualized and stored 521 by visualizing the final surgical plan from different perspectives to the user 522, 524, and by using database 523. Further analysis, discussion with the patient and/or transfer into the operating room is possible then. Step 520 thus depicts the decision finding whether the result of the calculation based on the previous selection of the surgical method and based on the description of the underlying individual case (by the surface representation and the received data about the planned intervention) is satisfactory or not. If the surgeon is not comfortable, a different surgical method can be selected and the previous steps beginning with the selection 513 can be repeated.

Figure 8:
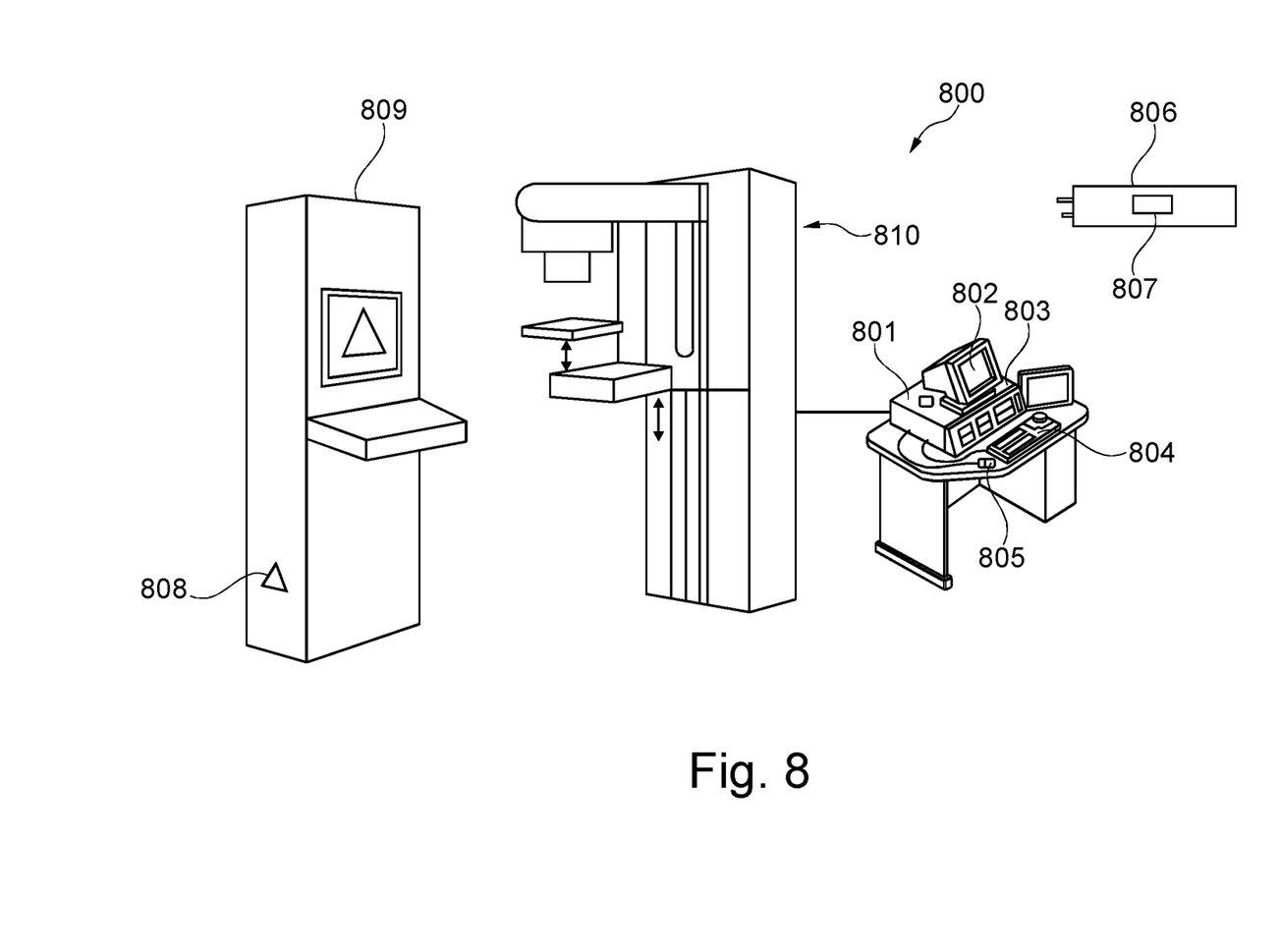
FIG. 8 schematically shows an apparatus according to another exemplary embodiment of the present invention.

In another exemplary embodiment, an apparatus is presented which also allows for such a procedure as described in the context of FIG. 5. Such an apparatus may be embodied as shown in FIG. 8. This apparatus is configured for calculating a surgical intervention plan and comprises a receiving unit (for receiving data of a patient's surface and data of a tumour location and/or tumour shape as an example of data about the planned intervention), a calculation unit, a display unit and a user interface. The calculation unit is configured for creating a surface representation of a part of the patient's body based on the received data and the user interface is configured for receiving a user input which is a selection of a first surgical method out of a plurality of parameterized surgical methods stored in a database. Moreover, the calculation unit is configured for adapting geometrical parameters of a surgical intervention plan based on the selected first surgical method. Also the display unit is configured for displaying the adapted surgical intervention plan based on the adapted geometrical parameters to a user. This apparatus may be seen as planning system for surgical interventions allowing the surgeon to do the pre-operative planning and drawing on the computer. It allows testing different surgical techniques by drawing them virtually onto the skin. The system automatically takes into account geometrical constraints of the surgical plans.

Figure 6:
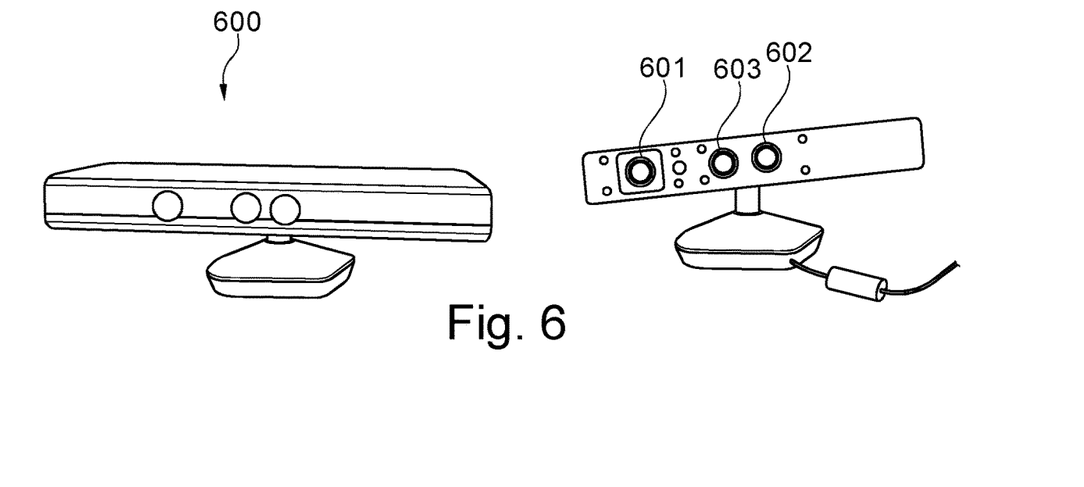
FIG. 6 schematically shows an apparatus comprising a scanner and a projector according to an exemplary embodiment of the present invention.

FIG. 6 shows a surface scanner 600 comprising a projector 601, which projects structured infrared (IR) light onto the scene and is an apparatus according to the present invention. It may be used in combination with the apparatus described in the context of FIGS. 1, 5, and 8, but may also be used independently thereof. The light of projector 601 which reflected back is then detected by the IR camera 602. By triangulation, the surface scene is calculated. Simultaneously, the RGB camera 603 operating in the visible light spectrum captures the surface colors of the patient's skin. If texture mapping is used, a complete 3D scene can be rendered. This example of a surface scanner is non-limiting and may be used in various different embodiments of the present invention as disclosed herein.

FIG. 7 shows a flow diagram and an apparatus 700 for calculating a surgical intervention plan and for projecting the desired plan back to the part of the patient which is analyzed. It is thus a planning and projection system for surgical interventions that allows the surgeon to do the pre-operative planning and drawing on the computer instead of on the patient. It allows testing different surgical techniques by drawing them virtually onto the skin. After a surgical plan has been selected, it can be used to transfer the plan onto the skin of the patient using marking. It should be noted that the shown process of FIG. 7 may also be carried out in part at different locations, i.e., on a plurality of different calculation units. Also the 3D scan can be just provided as data.

The apparatus 700 comprises a calculation unit 701 with means to visualize the planning, comprises means 704 to create a geometrical representation 705 of the patient's surface, and comprises means 702 to project the result of the planning back onto the patient. The calculation unit 701 may thus comprise a corresponding computer program element 706, i.e., a planning software element. In case of a planned tumour resection, the tumour position and/or the tumour resection margins can either be interactively defined or imported from a different workstation 707. Of course also other data about the planned intervention may be provided in this manner, If necessary, a pre-operative imaging dataset 708, e.g. MRI or CT, can be used. A sketch of the result of the beforehand described steps is shown with 709. Furthermore, a projection calculator 710 is comprised which is configured for calculating projection data for projecting the adapted surgical intervention plan onto the part of the patient's body based on the surface data 711. Thus, the system 700 facilitates transferring the projected and adapted surgical intervention plan onto the body of the patient by marking with e.g. a pen.

In a further specified example, a similar apparatus a combination of an optical surface scanner and a projector is used in order to capture the patient's surface and to project the planning result back to it. An example of a surface scanner is Microsoft's Kinect system may be used, originally marketed for gaming applications. Further, there are numerous examples for so called pico-projectors available of the shelf that can be used for this aspect of the present invention. Due to their small size, they can be easily integrated with surface scanning systems.

In the following, this further specified example as well as the embodiments shown in FIGS. 5 and 6 will be described in more detail. Regarding installation and calibration the following should be noted. The surface scanner and projector can be combined in a single housing with fixed relative position and orientation. Prior to using the system a calibration procedure can be used to determine the optical properties of the combined device. This calibration procedure is useful to allow for a geometrically correct projection of computer generated scenes onto real scenes. Calibration needs to be done only once in the factory. Further, the surface scanner captures geometrical as well as texture data and sends it to a calculation unit. For the step of generating planning input the following is disclosed. In an initial session the patient's surface and texture information can be recorded. The user may use the planning software to interact with the surface and texture information in order to create a surgical plan. if necessary, other information, e.g. X-ray mammograms or MR images can be retrieved from a database, e.g. 707 (FIG. 7) or 511 (FIG. 5), and can be used during planning. Furthermore, a transfer of the surgical plan is realized. In particular, in a second session prior to surgical intervention, the surgical plan is transferred to the patient. For this purpose the surface scanner can repeatedly scan the surface of the patient and sends the information to the computer. A projection calculator software may use this information together with the calibration information from the installation and calibration phase to calculate the projection of the surgical plan onto the patient's surface. The surgical plan can be seen by the surgeon on the surface and marked with a pen.

FIG. 8 schematically shows an apparatus 800 for calculating a surgical intervention plan. The apparatus comprises a calculation unit 801, a display unit 802, a receiving unit 803 for receiving data of a patient's surface and data of a planned surgical intervention. Moreover, interface 804 and mouse 805 are depicted in FIG. 8. Furthermore, the computer-readable medium 806 is embodied as a USB stick on which a computer program element 807 is stored. This computer program element is for calculating a surgical intervention plan in accordance with the present invention. Device 810 is a breast mammography device. Furthermore, a processing unit 809 is depicted in which a computer program element 808 is also stored. The apparatus 800 of FIG. 8 can be combined with a surface scanner and a projector as disclosed in the context of FIGS. 6 and 7 and may also be combined with the remotely activatable pen 901 as explained and described in the context of FIG. 9 in the following.

Figure 9:
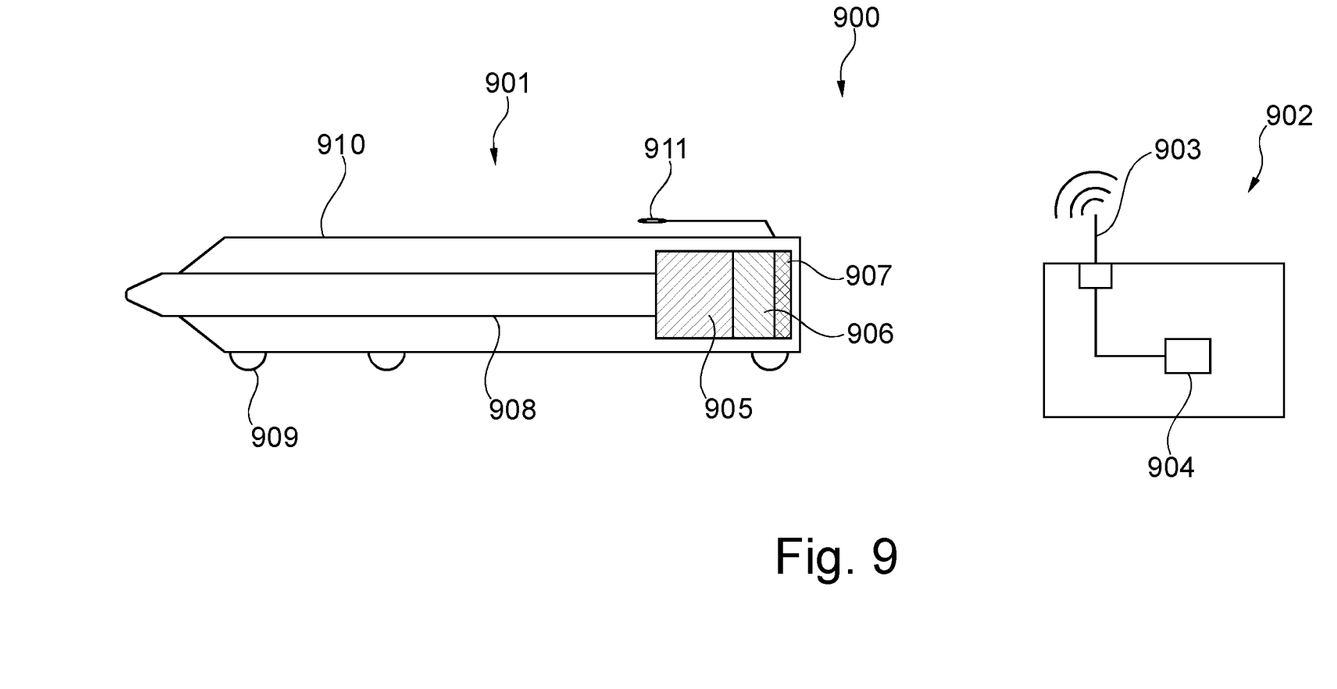
FIG. 9 schematically shows an apparatus with a remotely activatable pen in accordance with another exemplary embodiment of the present invention.

Before describing the apparatus and method underlying FIG. 9 the following should be noted for this subject matter. According to an exemplary embodiment of the present invention, an apparatus is presented herein which is configured for measuring the position of the pen, and which is configured for activating the pen when the measured position of the pen matches a line of the adapted surgical intervention plan. If desired, this functionality and features can be combined with the embodiments described before and hereinafter.

FIG. 9 shows a system for calculating a surgical intervention plan that comprises an apparatus with a sender and a control unit and the system comprises a remotely activatable pen which comprises a receiver. In detail, FIG. 9 schematically shows an apparatus 900 for calculating a surgical intervention plan and for remotely activating a pen for transferring the calculated plan onto the skin of the patient. Apparatus 902 may be embodied in analogy with the apparatuses as has been described before, for example, the apparatuses elucidated in FIGS. 5, 6, 7 and 8. In addition thereto, a sender 903 is comprised and also a control unit 904. The control unit 904 is configured for controlling the sender such that the sender sends an activation signal to the receiver 906 of the remotely activatable pen 901. A battery 907 may be provided in pen 901. Furthermore, a retraction unit 905 is depicted within the housing 910. 908 depicts the refill and 909 depicts an LED for a position measurement system. This active pen 901 has a mechanism to switch on and off its drawing capabilities. This can be realized with a retraction/protraction mechanism, which is built into the pen's housing and which retracts or protracts the refill, i.e. the ink containing part of the pen. The retraction/protraction mechanism can be triggered by the receiver unit in the pen which receives the signals from the sender 903 of apparatus 902. The signal can be transmitted either by infrared light, radio pulses or other appropriate activation signals. The battery in the pen provides the energy to operate the retraction/protraction mechanism and the receiver. However, also RFID technology may be used in this context. The position measurement system (not shown) measures the position of the pen and sends this to the control unit 904. The apparatus 902 compares the position with position stored in the surgical plan, in particular in the adapted surgical intervention plan. When the pen's position is sufficiently closed to one of the stored positions, the navigation system sends a signal to switch on the pen. When the pen's position is too far away, the navigation system sends a signal to switch off the pen. In this way, the pen can draw only at positions, which correspond to the predefined surgical intervention plan. The apparatus may also display the position of the pen within an image of the patient in order to allow easy positioning and aiming of the active pen. It should be noted, that also other methods of switching on and off the drawing capabilities of the pen shall be comprised by the present invention. For example, pressure may be used for such a switching process and also valves may be involved in the activation of the pen. Moreover, the receiver can be equipped with means to send the state of the pen, on and off, to the navigation system.

According to an exemplary embodiment of the present invention an apparatus is presented which is configured for measuring the position of the pen, and wherein the apparatus is configured for activating the pen when the measured position of the pen matches a line of the adapted surgical intervention plan.

This principle and interaction between this apparatus and the remotely activatable pen can also be gathered from the non limiting example of FIG. 9.

Moreover, according another exemplary embodiment of the present invention the pen comprises a retraction unit. This retraction unit may be remotely activatable based on the current position of the pen and based on the calculated surgical plan.

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. Any reference signs in the claims should not be construed as limiting the scope of the claims. The mere fact that certain measures are recited in mutually different dependent claims does not indicate that a combination of these measures cannot be used to advantage.

The invention claimed is:

1. A method comprising
scanning the part of the patient's body with a surface scanner;
capturing a photo of the part of the patient's body thereby providing the surface data of the patient's surface;
receiving the surface data of a patient's surface,
receiving intervention data about a planned surgical intervention, the intervention data including data representing a targeted object,
creating a surface representation of a part of the patient's body based on the received data of the patient's surface,
selecting a first surgical method out of a plurality of parameterized surgical methods stored in a database,
adapting geometrical parameters of a surgical intervention plan based on the selected first surgical method, the intervention data, and the surface representation, thereby calculating an adapted surgical intervention plan,
displaying the adapted surgical intervention plan to a user, and
transferring the adapted surgical intervention plan to the patient's surface to identify where incisions are to be made in accordance with this adapted surgical intervention plan.

2. The method of claim 1, further comprising retrieving a plurality of surgical methods from the database, wherein at least one geometrical constraint of the first surgical method is retrieved from the database, and wherein adapting the geometrical parameters of the surgical intervention plan is dependent upon the geometrical constraints of the first surgical method.

3. The method of claim 1, wherein creating the surface representation of the part of the patient's body comprises surface triangulation and texture mapping.

4. The method of claim 1, wherein the adapted surgical intervention plan is displayed to a user in form of at least a line of a future skin incision in the created surface representation of the part of the patient's body.

5. The method of claim 4, further comprising:
receiving a user input configured to trigger a change of the geometrical parameters of the surgical intervention plan, and
adapting the geometrical parameters of the surgical intervention plan based on the received user input.

6. The method of claim 1, further comprising:
selecting a second surgical method out of the plurality of surgical methods stored in the database,
adapting the geometrical parameters of the surgical intervention plan based on the second selected surgical method, and
displaying the surgical intervention plan to a user in form of at least a line of a future skin incision shown in the created surface representation of the patient's surface.

7. The method of claim 1, further comprising interactively defining a targeted object's position and/or a targeted object resection margin or importing a targeted object's position and/or a targeted object's shape and/or a targeted object resection margin from a workstation.

8. The method of claim 1, wherein transferring the adapted surgical implementation plan includes projecting the adapted surgical intervention plan onto the patient's surface.

9. The method of claim 1, wherein transferring the adapted surgical implementation plan includes sending an activation signal to a remotely activatable marking pen thereby activating the pen to mark the patient surface based on the adapted surgical intervention plan.

10. The method of claim 9, further comprising:
measuring a position of the pen on a surface of the patient, and
activating the pen if the measured position of the pen corresponds to a line of the adapted surgical intervention plan.

11. The method of claim 8, including placing photosensitive material on the patient's surface, and wherein the projecting causes select activation of the photosensitive material.

12. An apparatus comprising:
a surface scanner that scans a surface of a part of a patient's body to provide surface data of the patient's surface,
a receiving circuit that receives the surface data of the patient's surface and intervention data of a planned surgical intervention, the intervention data including data representing a targeted object,
a calculation circuit,
a display device,
an interface circuit,
a database, and
a transfer device,
wherein the calculation circuit is configured to create a surface representation of a part of the patient's body based on the surface data,
wherein the interface circuit is configured to receive a user input comprising a selection of a first surgical method out of a plurality of parameterized surgical methods stored in the database,
wherein the calculation circuit is configured to adapt geometrical parameters of a surgical intervention plan based on the selected first surgical method, the intervention data, and the surface representation; the calculation circuit further being arranged to calculate an adapted surgical intervention plan in accordance with the adapted geometrical parameters,
wherein the display device is configured to display the adapted surgical intervention plan to a user, and
wherein the transfer device is configured to transfer the adapted surgical intervention plan to the patient's surface to identify where incisions are to be made in accordance with this adapted surgical intervention plan.

13. The apparatus of claim 12, wherein the transfer device includes a projection device that is configured to project the adapted surgical intervention plan onto the surface of the part of the patient's body.

14. The apparatus of claim 12, wherein the apparatus includes a controller circuit that is configured to activate a remotely activatable pen to mark the patient's surface based on the adapted surgical intervention plan.

15. The apparatus of claim 14, wherein the apparatus includes a sensor circuit that is configured to determine a position of the pen on a surface of the patient, and wherein the controller circuit activates the pen if the determined position of the pen corresponds to a line of the adapted surgical intervention plan on the patient's surface.

16. The apparatus of claim 12, wherein the calculation circuit creates the surface representation of the part of the patient's body using surface triangulation and texture mapping.

17. The apparatus of claim 12, wherein the display device displays the adapted surgical intervention plan in form of at least a line of a future skin incision in the created surface representation of the part of the patient's body.

* * * * *